United States Patent [19]

Vashi et al.

[11] Patent Number: 4,723,029

[45] Date of Patent: Feb. 2, 1988

[54] ORGANIC ACID-SUBSTITUTED GUANIDINE ANTHELMINTICS

[75] Inventors: Dhiru B. Vashi, Wharton; Jeffrey N. Clark, New Egypt; Neil A. Lindo, New Providence, all of N.J.

[73] Assignee: Schering Corporation, Kenilworth, N.J.

[21] Appl. No.: 535,019

[22] Filed: Sep. 23, 1983

[51] Int. Cl.$^4$ ............................................ C07C 149/43
[52] U.S. Cl. ................................. 560/13; 514/114; 514/115; 514/119; 514/483; 514/485; 514/488; 514/517; 514/562; 514/563; 514/564; 558/29; 558/30; 558/172; 558/176; 558/169; 558/170; 558/174; 560/9; 560/25; 560/29; 560/30; 560/32; 560/24

[58] Field of Search .................. 560/9, 13, 25, 26, 27, 560/29; 424/300, 303, 211; 260/457, 938, 458 C, 502.50, 510; 558/30, 172

[56] References Cited

U.S. PATENT DOCUMENTS

| | | | |
|---|---|---|---|
| 4,217,358 | 8/1980 | Haugwitz | 560/13 |
| 4,246,260 | 1/1981 | Kolling | 560/13 |
| 4,348,406 | 9/1982 | Nafissi-Varchei | 424/300 |
| 4,406,893 | 9/1983 | Nafissi-Varchei | 560/13 |
| 4,435,398 | 3/1984 | Nafissi-Varchei | 560/13 |

*Primary Examiner*—Michael L. Shippen
*Attorney, Agent, or Firm*—John J. Maitner; Stephen I. Miller; James R. Nelson

[57] ABSTRACT

This invention relates to organic acid-substituted guanidine compounds. Also disclosed are methods for preparing the compounds, compositions containing them, and methods for their use as anthelmintics.

4 Claims, No Drawings

ORGANIC ACID-SUBSTITUTED GUANIDINE ANTHELMINTICS

This invention relates to novel organic acid substituted guanidine compounds, to methods for preparing and using them, and to compositions containing them. Compounds of the invention have anthelmintic activity.

DETAILED DESCRIPTION

The compounds of the present invention are represented by the formula

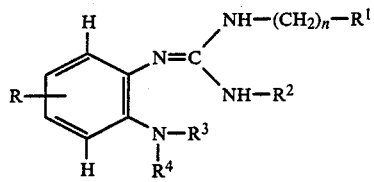

and the pharmaceutically acceptable salts thereof, wherein

R is a hydrogen, $-OR^5$, $-S(O)_mR^5$,

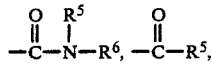

halogen or $-CF_3$;
$R^1$ is $-SO_3H$, $-OSO_3H$, $-COOH$, $-PO_3H_2$, or $-OPO_3H_2$;
$R^2$ is hydrogen,

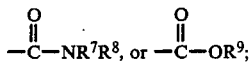

$R^3$ and $R^4$ are independently hydrogen loweralkyl, loweralkylcarbonyl, loweralkoxycarbonyl, loweralkoxyloweralkyl, phenyl or substituted phenyl, benzoyl or substituted benzoyl, phenoxycarbonyl or substituted phenoxycarbonyl (wherein there are 1, 2 or 3 substituents on the substituted phenyl, substituted benzoyl or substituted phenoxycarbonyl independently selected from halogen, lower alkyl, loweralkoxy, trifluoromethyl, and haloloweralkyl), carboxy-substituted lower alkyl, or sulfo-substituted lower alkyl;
$R^5$ and $R^6$ are independently hydrogen, lower alkyl, loweralkoxyloweralkyl, hydroxyloweralkyl, cycloloweralkyl, phenyl or substituted phenyl, benzyl or substituted benzyl (wherein there are 1, 2 or 3 substituents on the substituted phenyl or substituted benzyl independently selected from halogen, lower alkyl, lower alkoxy, haloloweralkyl or loweralkoxyloweralkyl) or 5 or 6 membered heterocycles having 1 or 2 heteroatoms independently selected from oxygen, nitrogen and sulfur;
$R^7$, $R^8$ and $R^9$ are independently hydrogen, loweralkyl, loweralkoxyloweralkyl, hydroxyloweralkyl, phenyl or substituted phenyl, and benzyl or substituted benzyl (wherein there are 1, 2 or 3 substituents on the substituted phenyl or substituted benzyl independently selected from halogen, lower alkyl, lower alkoxy, haloloweralkyl, or loweralkoxy, haloloweralkyl, or loweralkoxyloweralkyl);
n is 1 to 6; and
m is 0, 1 or 2; provided that when $R^2$ is

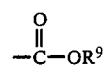

wherein $R^9$ is lower alkyl, R is $-OR^5$ or loweralkylthio and $R^1$ is $-COOH$, the group

is not $NH_2$ or $NHR^4$ wherein $R^4$ is lower alkylcarbonyl or benzoyl.

As used herein, "lower alkyl" means straight or branched alkyl chains of 1 to 6 carbon atoms, e.g. methyl, ethyl, n-propyl, n-butyl, iso-butyl, and hexyl. Similarly, "lower alkoxy" means alkoxy groups having 1 to 6 carbon atoms, e.g. methoxy, ethoxy, propoxy, iso-butoxy, and pentoxy. "Cycloloweralkyl" means alkyl rings of 3 to 6 members, i.e. cyclopropyl, cyclobutyl, cyclopentyl, and cyclohexyl. "Halogen" means fluorine, chlorine, bromine and iodine. "Haloloweralkyl" means loweralkyl groups substituted by 1 to 3 halogen atoms, e.g. trifluoromethyl, dichloromethyl and chloroethyl.

Examples of heterocycles defined in $R^3$ and $R^4$ are pyridine, furan, thiophene, pyrimidine, piperazine and thiazole. All positional isomers are contemplated, e.g. 2-, 3- and 4-pyridine, 2- and 3-furan.

The pharmaceutically acceptable salts contemplated include metal salts, e.g. alkali and alkali earth metal salts such as sodium, potassium and calcium, and other physiologically acceptable salts, e.g. trisamine, alkyl ammonium salts such as N-methylglucamine, ethanolamine, diethanolamine, triethanolamine, pyridinium and procaine, and tretralkylammonium salts such as those produced with tetramethylammonium or tetraethylammonium ions.

Also included within the scope of the invention are the tautomers at the guanidine group,

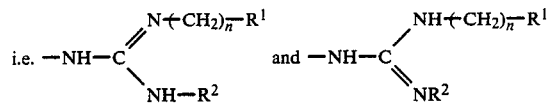

Preferred compounds are those wherein R is $-S(O)_mR^3$ and wherein the loweralkylthio, sulfinyl or sulfonyl substituent is in the 5-position of the phenyl ring. Also preferred are compounds wherein $R^1$ is

A third group of preferred compounds are those wherein $R^2$ is $-SO_3H$ and n is 2.

The compounds of this invention can be prepared as follows according to procedures generally known in the art for preparing similar compounds.

A convenient intermediate for the preparation of compounds of formula I is a N-lower-alkoxycarbonyl-N'-[(2-nitro-(4- or 5-)substituted)phenyl]-N''-(alkylacid)guanidine, i.e. a compound of the formula

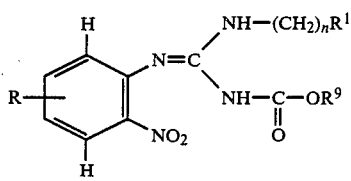

N-alkoxycarbonyl compounds of formula II can be hydrolyzed according to well known procedures (e.g. with a base such as sodium hydroxide in a solvent such as water or methanol) to prepare the corresponding (alkyl acid)guanidines (i.e. the

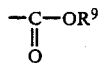

group is replaced by H).

(Alkylacid)guanidines can be treated with a diloweralkylcarbamyl chloride, e.g. dimethyl carbamyl chloride, according to techniques known in the art to obtain the corresponding N-[diloweralkylcarbamyl]-N'-[(2-nitro-(4- or 5-)substituted)phenyl]-N''-(alkylacid)guanidine.

N-[loweralkylcarbamyl]homologs, e.g. methylcarbamyl compounds, can be prepared by treating (alkylacid)guanidines with potassium cyanate followed by alkylation with di-loweralkyl sulfate, e.g. dimethylsulfate, or lower alkyl halide, e.g. methyl chloride or methyl bromide. Alternatively, alkylcarbamyl compounds can be prepared by treating (alkylacid)guanidines or the sodium salts thereof with alkyl isocyanate.

N-[carbamyl] compounds can also be prepared from (alkylacid)guanidines by treatment with potassium cyanate followed by treatment with acid such as hydrochloric, acetic or sulfuric acid.

2-nitro compounds of formula II can be used as intermediates in well known reactions to prepare compounds of the present invention, i.e. compounds wherein the substitutent at the 2-position in the phenyl ring is of the formula $-NR^3R^4$.

For example, (2-lower alkylamino-(4- or 5-)substituted phenyl) compounds may be prepared by hydrogenation (catalytic or chemical) of compounds of formula II, followed by alkylation with di-lower alkyl sulfate or lower alkyl halide as described above.

Similarly, the lower alkylamino compounds prepared as in the immediately preceeding paragraph can be further alkylated by di-lower alkyl sulfate or lower alkyl halide to obtain the (2-di-loweralkylamino-(4- or 5-)substituted)phenyl compounds of formula I.

Alternatively, the conversion of the 2-nitro compound to the corresponding 2-alkylamino or 2-dialkylamino compound can be carried out by hydrogenating the 2-nitro compound using an aliphatic aldehyde and platinum oxide as catalyst. For example, using formaldehyde in a 1:1 molar ratio to the nitro compound will yield the methylamine derivative, and using formaldehyde in a 2:1 molar ratio will yield the dimethylamine compound.

Compounds of formula I wherein one of $R^3$ and $R^4$ is lower alkyl and the other of $R^3$ and $R^4$ is lower alkoxycarbonyl can be prepared by the reaction of the appropriate (2-loweralkylamino-(4- or 5-)substituted)phenyl compound with the appropriately substituent acyl halide, e.g. methyl chloroformate, ethyl chloroformate, butyl chloroformate, 4-chlorophenyl chloroformate, 3-methylphenyl chloroformate, or 4-methoxyphenyl chloroformate.

Compounds of formula I wherein $R^3$ and $R^4$ are lower alkyl carbonyl or optionally substituted benzoyl can be prepared by the reaction of the appropriate carbonyl chloride (e.g. benzoyl chloride or acetyl chloride) with the desired (2-amino-(4 or 5)substituted)phenyl compounds according to procedures known in the art.

Compounds of formula I wherein $R^3$ or $R^4$ is sulfolower alkyl or carboxy-lower alkyl are prepared by the reaction of the corresponding Ω-halo-alkyl sulfonic- or carboxylic acid salt with the intermediate formed by the hydrogenation of compounds of formula II. For example, the reaction of a hydrogenated compound of formula II with 2-chloroethane sulfonic acid sodium salt produces the taurine derivative (i.e. the N'-[(2-sulfonic acid ethylamino-(4- or 5-)substituted)phenyl]compounds).

It will be apparent to those skilled in the art that successive modifications of compounds of formula II may be used to prepare compounds of formula I.

Compounds of formula II are prepared by treating an appropriately substituted 1-nitro-2-amino benzene with a carboalkoxyisothiocyanate, followed by reacting the resulting product with an Ω-aminoalkyl acid (e.g. taurine, 3-amino 1-propane sulfonic acid, 2-aminoethylphosphonic acid or 4-aminobutyrate) and a base such as sodium hydroxide. A typical reaction scheme is shown below:

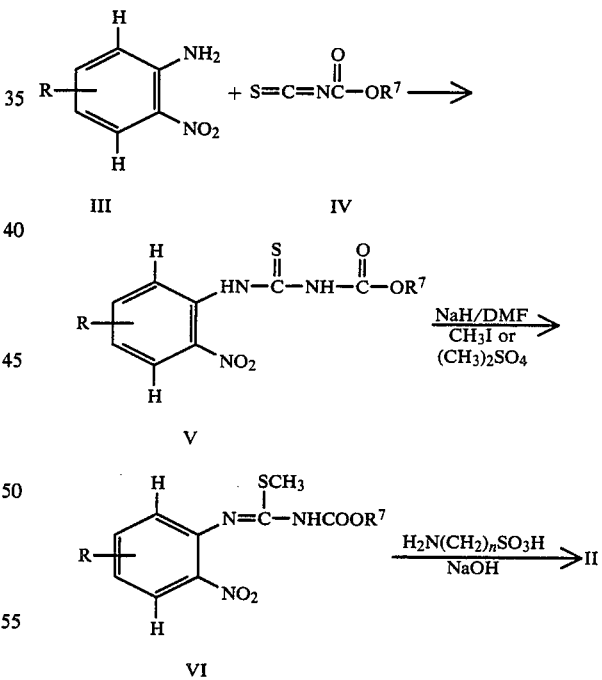

Compounds of formula III are either known in the art or may be prepared by methods well known to those skilled in the art.

Compounds of formula I can be prepared without using the intermediate of formula II. For example, 3,4-dinitrochlorobenzene may be treated with liquid ammonium in a solvent such as ethanol to obtain 2-nitro-5-chloroaniline, which may then be treated with acetic anhydride in a solvent such as pyridine at 0°–5° C. to yield 2-nitro-5-chloroacetanilide. The 2-nitro-5-chloro acetanilide may then be converted to the corresponding 2-dialkylamino-5-chloroacetanilide by hydrogenating the nitro compound using platinum on carbon as catalyst in the presence of an aliphatic aldehyde (2:1 molar ratio to the nitro compound). The acetanilide can be hydrolyzed with a reagent such as sodium methoxide in a solvent such as methanol to give the corresponding 2-dialkylamino-5-chloroaniline. The chloroaniline can be treated with an appropriate reagent to give a 2-dialkylamino-5-substituted-aniline, e.g. the chloroaniline reacted with 1-propanethiol and sodium hydroxide in dimethylformamide/water at room temperature will yield 2-dialkylamino-5-propylthioaniline. This aniline may then be treated as the compound of formula III on page 5 to obtain a compound of formula I.

Preferred compounds of formula I wherein R is —S(O)$_m$R$^3$ may be prepared by well known procedures from the corresponding —SR$^3$ compounds by treating the thio substituent with an oxidizing agent such as m-chloroperbenzoic acid, sodium m-periodate or hydrogen peroxide in acetic acid. Amino groups in the starting materials may be protected during the oxidation by the addition of a reagent such as trifluoroacetic acid. Treatment with one equivalent of oxidizing agent will yield the —SOR$^3$ (sulfinyl) compound while treatment with two equivalents will yield the —SO$_2$R$^3$ compound (sulfonyl). This oxidation may be carried out at one of several stages in the preparation of the compound as shown below, wherein the preparation of the sulfinyl compound is described.

Metal salts, alkyl ammonium salts and other pharmaceutically acceptable salts may be prepared according to methods well known to those skilled in the art.

The following examples illustrate the preparation of compounds and compositions of this invention.

EXAMPLE 1

N-Methoxycarbonyl-N'-[(2-dimethylamino-5-propylthio)phenyl]-N''-(2-ethyl sulfonic acid)guanidine Combine N-methoxycarbonyl-N'-[(2-nitro-5-propylthio)phenyl]-N''-(2-ethyl sulfonic acid)guanidine (4.2 g) Raney Nickel (1.0-2.0 g) and formaldehyde (0.6 g) in 95% ethanol (100 ml) in a pressure bottle and catalytically reduce the mixture at an initial pressure of 3 atm. hydrogen. After 0.03M to 0.04M hydrogen is absorbed, stop the reduction and filter off the catalyst. Evaporate the filtrate to dryness to obtain the title compound.

EXAMPLE 2

N-((2-Amino-5-propylthio)phenyl]-N'-(2-ethyl sulfonic acid)guanidine

Combine the product of Example 1 with sodium hydroxide in water and reflux for 4 hours. Cool the resulting solution and acidify to pH 1-2 with 10N aqueous hydrochloric acid. Filter the resulting precipitate, wash with cold water (3×) then methanol (2×) and dry to obtain the title compound.

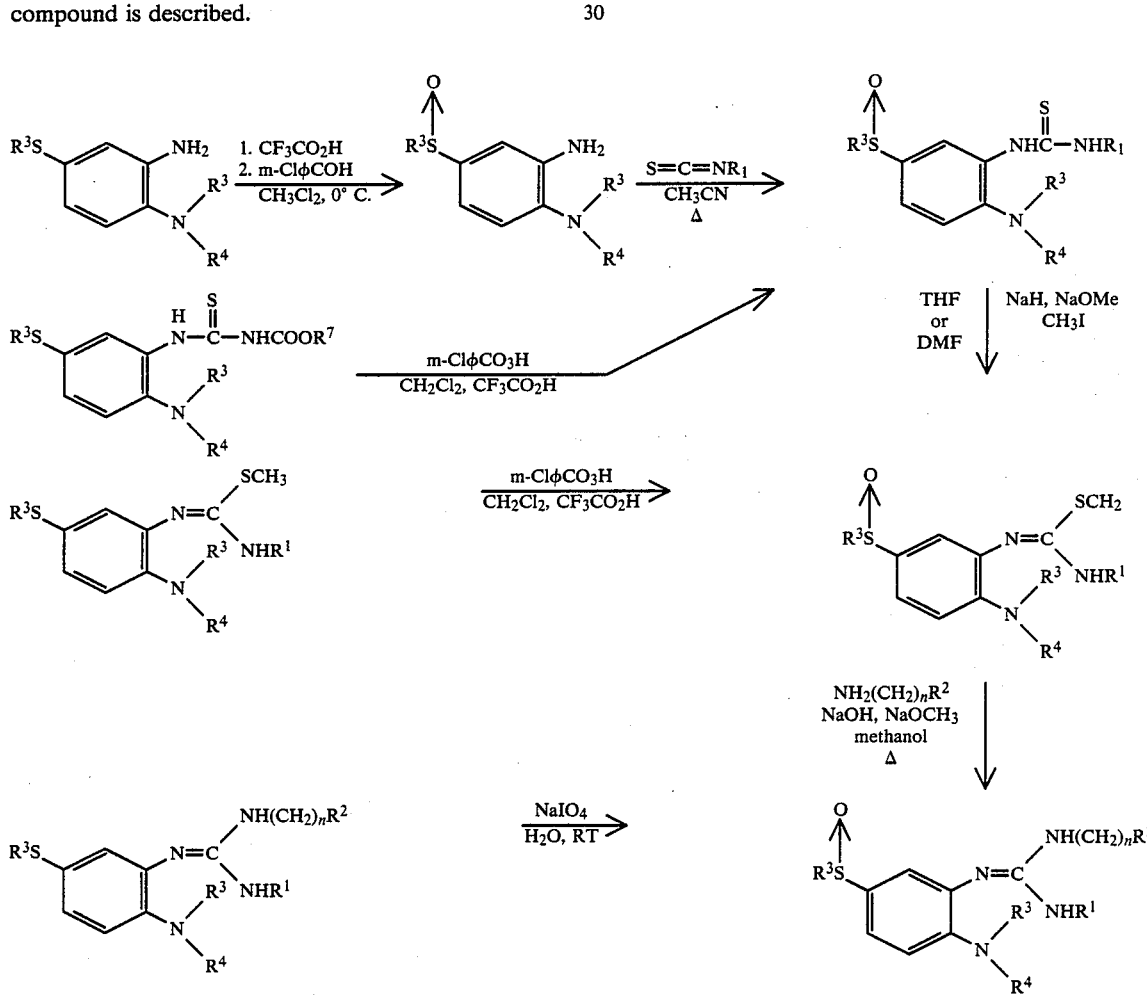

EXAMPLE 3

N-Methoxycarbonyl-N'-[(2-dimethylamino-5-propylsulfinyl)phenyl]-N''-(2-ethane sulfonic acid)guanidine A. In the pressure bottle of an apparatus for catalytic reduction, combine N-methoxycarbonyl-N'[(2-nitro-5-propylthio)phenyl]-S-methyl isothiourea (3.4 g), formaldehyde (0.6 g), 95% ethanol (100 ml) and Raney nickel (1.0 to 2.0 g), evacuate the bottle and apply an initial pressure of 3 atm. of hydrogen. After 0.03 to 0.04M hydrogen is absorbed (1-2 hours), stop the reduction and filter off the catalyst. Evaporate the resultant filtrate to dryness and recrystallize the resultant residue to obtain N-methoxycarbonyl-N'-[(2-dimethylamino-5-propylthio)phenyl]-S-methyl isothiourea.

B. Slurry the product of step A (1.7 g) in ether (50 ml), add m-chloroperbenzoic acid (1.1 g of an 85% solution in 20 ml ether) and stir at room temperature 20 minutes. Extract the resultant solution with 5% aqueous sodium bicarbonate solution (3×50 ml), dry the organic phase over magnesium sulfate and evaporate the solvent. Purify the resultant crude product by chromatography and recrystallize the chromatographed product from ether to obtain N-methoxycarbonyl-N'-[(2-dimethylamino-5-propylsulfinyl)phenyl]-S-methyl isothiourea.

C. To a solution of sodium taurine (1.75 g) in water (10 ml) at room temperature, add a solution of the product of step B (3.3 g) in methanol (100 ml) and stir for several days. Filter the solid and wash with acetone. Add the solid to boiling methanol, filter the excess insoluble sodium taurine and refrigerate the methanol solution. Filter the resultant precipitate and dry to obtain N-methoxycarbonyl-N'-[(2-dimethylamino-5-propylsulfinyl)-phenyl]-N''-(2-ethyl sulfonic acid)guanidine sodium salt. To obtain the free Zwitterion, dissolve the sodium salt in water, adjust to pH 1.5 with acid (e.g. hydrochloric) and filter the resultant solid. Wash the resultant solid with acetone and dry to obtain the title compound.

Using the methods described above, the following compounds also can be prepared:

N-methoxycarbonyl-N'-[(2-methylamino-(4 or 5)-propylthio)phenyl]-N''-(2-ethyl sulfonic acid)guanidine;

N-methoxycarbonyl-N'-[(2-dimethylamino-(4 or 5)-propylthio)phenyl]-N''-(2-ethyl sulfonic acid)guanidine;

N-methoxycarbonyl-N'-[(2-sulfonic acid ethyl)amino-(4or 5)-propylthio)-phenyl]-N''-(2-ethyl sulfonic acid)guanidine;

N-methoxycarbonyl-N'-[(2-acetamido-(4 or 5)-propylthio)phenyl]-N''-(2-ethyl sulfonic acid)guanidine;

N-(4-chlorobenzyloxycarbonyl)-N'-[(2-carboxyethylamino(4or 5)-propylthio)phenyl]-N''-(2-ethyl sulfonic acid)guanidine;

N-[(N'''methyl-N'''-benzyl)carbamyl]-N'-[(2-amino-(4 or 5)-propylthio)phenyl]-N''-(2-ethyl sulfonic acid)guanidine;

N-[(N'''methyl-N'''-ethyl)carbamyl]-N'-[(2-amino-(4 or 5)-propoxy)phenyl]-N''-(2-ethyl sulfonic acid)guanidine;

N-(4-chlorobenzyloxycarbonyl)-N'-[2-amino-(4 or 5)-chlorophenyl]-N''-(2-ethyl phosphoric acid)guanidine;

N-dimethylcarbamyl-N'-[(2-amino-(4 or 5)propoxy)phenyl]-N''-(2-ethyl hydrogen phosphate)guanidine;

N-methoxycarbonyl-N'-[(2-amino-(4 or 5)-(3-hydroxy)-propyloxy)phenyl]-N''-(2-ethyl sulfonic acid)guanidine;

N-carbamyl-N'-[(2-amino-(4 or 5)-amidophenyl]-N''-(2-ethyl sulfonic acid)guanidine;

N-methoxyethylcarbamyl-N'-[(2-amino-(4 or 5)-(4-acetylphenyl)]-N''-(2-ethyl sulfonic acid)guanidine;

N-methoxycarbonyl-N'-[(2-amino-(4 or 5)-propylsulfonyl)phenyl]-N''-(2-ethyl sulfonic acid)guanidine;

N-ethoxycarbonyl-N'-[(2-methylamino-(4 or 5)-cyclopropylthio)phenyl]-N''-(2-ethyl sulfonic acid)guanidine;

N-carbamyl-N'-[(2-dimethylamino-(4 or 5)-(3-ethoxy)-propylthio)phenyl]-N''-(2-ethyl hydrogen sulfate)-guanidine;

N-carbamyl-N'-[(2-amino-(4 or 5)-phenylthio)phenyl]-N''-(2-ethyl sulfonic acid)guanidine;

N-(2-hydroxyethylcarbamyl)-N'-[(2-acetamido-(4 or 5)-propylthio)phenyl]-N''-(2-ethyl sulfonic acid)guanidine;

N-methoxyethylcarbamyl-N'-[(2-methoxycarbonylamino-(4 or 5)-4-chlorophenylthio)phenyl]-N''-(2-ethyl sulfonic acid)guanidine;

N-phenoxycarbonyl-N'-[(2-(2-methoxyethyl)amino-(4 or 5)methoxybenzylthio)phenyl]-N''-(2-ethyl sulfonic acid)guanidine;

N-methoxycarbonyl-N'-[(2-(N''''-anilino)-(4 or 5)-butylsulfinyl)phenyl]-N''-(2-ethyl sulfonic acid)guanidine;

N-[(2-benzamido-(4 or 5)-propylthio)phenyl]-N'-(2-ethyl sulfonic acid)guanidine;

N-methylcarbamyl-N'-[(2-(N''''-4-chloroanilino)-(4 or 5)propylthio)phenyl]-N''-(2-ethyl sulfonic acid)guanidine; and N-dimethylcarbamyl-N'-[(2-(4-methoxybenzamido)-(4 or 5)propylthio)phenyl]-N''-(2-ethyl carboxylic acid)guanidine.

The compounds of the present invention are useful in combatting helminthiasis, i.e. in treating animals, including humans, suffering from an infestation of parasitic worms, for example, roundworms, hookworms, whipworms or tapeworms, by administering to the host animal a therapeutic amount of a compound of the present invention.

The compounds of this invention exhibit significant anthelmintic effects when administered to a host (e.g. a human, swine, dog, bird or ruminant) at doses as low as about one milligram per kilogram of body weight to about one hundred fifty milligrams per kilogram in a single day dosing or over several days, according to techniques well known in the art. A preferred method is to administer the compound at 5 to 25 milligrams per kilogram in a single dose.

The optimum dose for each species of animal and for each type of parasite can readily be determined by one skilled in the art of using standard techniques such as the Modified McMaster Egg Counting Technique as described by H. B. Whitlock and H. McL. Gordon, J. Council Scientific Industrial Research (Australia) 12, p. 50, 1939 and H. B. Whitlock, J. Council Scientific Research (Australia) 21, p. 177, 1948.

From these, and similar tests, anthelmintic efficacy is assessed by determining the number of eggs in feces passed on the days following treatment with the compound compared with pretreatment days. Based on experimentation, proper dosages for curing various infections can be determined.

Compounds of this invention may be administered in various formulations well known to those skilled in the human and veterinary medical arts, e.g., suspensions, solutions, capsules, tablets and injectable preparations. In addition, for veterinary use, the compounds may be administered as feed or drinking water additive preparations.

For injectable preparations, the active ingredient is admixed with suitable sterile carriers such as sterile water and isotonic saline solution.

Suitable clinical formulations containing the compounds of this invention can be administered orally in the form of tablets, capsules, elixirs and the like. The active compound is compounded with inert carriers such as, for example, gums, starches and sugars or it may be incorporated into gelatin capsules or formulated into elixirs which have the advantage of being amenable to manipulations in flavor by the addition of flavoring agents.

Anthelmintic formulations particularly useful for, but not limited to, veterinary use comprise the compounds of this invention in ready to use liquid suspensions or wettable or water-dispersible powders which are mixed with water prior to use.

The following examples show particularly useful formulations. In the examples, the term "Drug" refers to N-(methoxycarbonyl)-N'-[(2-dimethylamino-5-propylthio)phenyl]-N"-(2-ethyl sulfonic acid)guanidine. It will be appreciated by those skilled in the art that an equivalent amount of another compound of formula I may be substituted for the named compound.

A. Liquid-suspension formulation:

A liquid-suspension formulation may contain from 50 to 55% w./v. (grams/liters) of the active compound together with a dispersing agent and stabilizing agent. A typical formulation is as follows:

| Drug | 50 to 55 parts by weight |
|---|---|
| Dispersing agent | ½ to 2 parts by weight |
| Stabilizing agent | 1 to 3 parts by weight |
| Preservative | as required |
| Water | Sufficient to make 100 volumes. |

Suitable dispersing agents are those containing sulphonate groups, for example sodium lignin sulphonate, or the sulphonated phenol or naphthol formaldehyde polymers. Bentonite may be employed as the stabilizing agent, although it is possible to use such protective colloids as carboxymethyl cellulose, sodium alginate and the like. The formulations can be prepared by mixing the active compound and water containing dissolved dispersing agents very vigorously by means of suitable mechanical mixing equipment.

B. Powder formulation:

A wettable or water-dispersible powder formulation may contain about 90 to 95% w./w. of the active compound together with a wetting agent and dispersing agent. A diluent such as kaolin can also be added if a concentration below about 98% w./w. is required. An anti-foaming agent and, in some cases, a stabilizing agent may be present. A typical formulation is as follows:

| Drug | 90 to 95 parts by weight |
|---|---|
| Wetting agent | ½ to 4 parts by weight |
| Stabilizing agent | 0 to 2 parts by weight |
| Anti-foaming agent | 0.01 to 1 by weight |
| Water | 0 to 5 by weight |

Suitable wetting agents are the non-ionic alkylphenolethylene oxide adducts, such as an octylphenol or nonylphenol condensed with ten moles of ethylene oxide, or anionic materials, such as the synthetic aryl alkyl sulphonates, or sodium dibutyl naphthalene sulphonate. In general, about 1% w./w. wetting agent is required. The anti-foaming agent employed may be either a silicone or such materials as ethyl hexanol, octanol and the like; and the stabilizing agent may be chosen from bentonite or the water-soluble gums as discussed above. Wettable or water-dispersible powder formulations are prepared by careful and adequate mixing of the active compound with other ingredients with or without the addition of some water using typical powder blending equipment such as a ribbon blender. The powder is stirred into water by the user before application in the field.

| C. Tablet formulation | Grams per 1000 tablets |
|---|---|
| Drug | 200.0 |
| Lactose | 90.0 |
| Dicalcium phosphate, hydrous | 122.5 |
| Polyvinylpyrolidone | 25.0 |
| Polyethyleneglycol 1500 | 7.5 |
| Corn Starch | 50.0 |
| Magnesium Stearate | 5.0 |
| | 500.0 |

Mix the active compound, the lactose and the diacalcium phosphate. Dissolve the polyethyleneglycol 1500 and the polyvinylpyrrolidone in approximately 20 ml of water. Granulate the powder blend with the water solution, adding additional water if necessary, to product a damp mass. Pass the wet granulation through a 12 mesh screen; spread on trays and air dry at 35° C. Blend the dry granulates with the starch and the magnesium stearate. Compress into 500 mg tablets.

| D. Capsule formulation | Grams per 1000 capsules |
|---|---|
| Drug | 200.0 |
| Lactose | 198.0 |
| Magnesium Stearate | 2.0 |
| | 400.0 |

Blend the ingredients and fill into hard gelatine capsules

| E. Injectible formulation | mg/ml |
|---|---|
| Drug | 50.0 |
| Polyethylene Glycol 400 | 500.0 |
| Dimethyl Acetamide | 300.0 |
| Benzyl Alcohol | 20.0 |
| Water for Injection to q.s. | 1.0 ml |

Combine the above ingredients using standard techniques.

We claim:

1. A compound represented by the formula

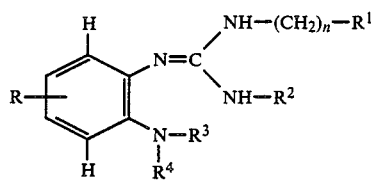

and the pharmaceutically acceptable salts thereof, wherein

R is $-S(O)_mR^5$ and is at the 5-position on the phenyl ring;

$R^1$ is $-SO_3H$, $-OSO_3H$, $-PO_3H_2$, or $-OPO_3H_2$;

$R^2$ is

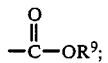

$R^3$ and $R^4$ are loweralkyl;

$R^5$ is lower alkyl;

$R^9$ is hydrogen, loweralkyl, loweralkoxyloweralkyl, hydroxyloweralkyl, phenyl or substituted phenyl, and benzyl or substituted benzyl (wherein there are 1, 2 or 3 substituents on the substituted phenyl or substituted benzyl independently selected from halogen, lower alkyl, lower alkoxy, haloloweralkyl, or loweralkoxyloweralkyl);

n is 1 to 6; and m is 0.

2. A compound of claim 1 which is N-methoxycarbonyl-N'-[(2-dimethylamino-5-propylthio)phenyl]-N-"-(2-ethyl sulfonic acid)guanidine.

3. A compound of claim 1 which is N-methoxycarbonyl-N'-[(2-dimethylamino-5-propylthio)phenyl]-N"-(3-propylsulfonic acid)guanidine.

4. A compound of claim 1 wherein $R^9$ is lower alkyl.

* * * * *